US010624979B2

(12) United States Patent
Brockschmidt et al.

(10) Patent No.: US 10,624,979 B2
(45) Date of Patent: Apr. 21, 2020

(54) SYSTEMS AND METHODS FOR OPERATING A LIGHT SYSTEM

(71) Applicant: The Boeing Company, Chicago, IL (US)

(72) Inventors: Arthur E. Brockschmidt, Renton, WA (US); Jamie J. Childress, Seattle, WA (US); Karen L. Hills, Seattle, WA (US); Teresa A. King, Seattle, WA (US)

(73) Assignee: The Boeing Company, Chicago, IL (US)

( * ) Notice: Subject to any disclaimer, the term of this patent is extended or adjusted under 35 U.S.C. 154(b) by 111 days.

(21) Appl. No.: 15/633,085

(22) Filed: Jun. 26, 2017

(65) Prior Publication Data
US 2018/0369439 A1 Dec. 27, 2018

(51) Int. Cl.
*A61L 2/10* (2006.01)
*H05B 37/02* (2006.01)
(Continued)

(52) U.S. Cl.
CPC .................. *A61L 2/26* (2013.01); *A61L 2/10* (2013.01); *A61L 2/24* (2013.01); *A61L 9/20* (2013.01);
(Continued)

(58) Field of Classification Search
CPC ..... A61L 2/10; A61L 2/24; A61L 2/26; A61L 9/20; A61L 2202/11; A61L 2202/14;
(Continued)

(56) References Cited

U.S. PATENT DOCUMENTS 5,483,127 A  1/1996 Widmayer
5,705,898 A  1/1998 Yamashita et al.
(Continued)

FOREIGN PATENT DOCUMENTS

DE  198 24 423  12/1999
JP  H08 31585  2/1996
(Continued)

OTHER PUBLICATIONS

Extended European Search Report prepared by the European Patent Office in application No. EP 18 17 2465 dated Jan. 11, 2019.
(Continued)

*Primary Examiner* — Jimmy T Vu
(74) *Attorney, Agent, or Firm* — McDonnell Boehnen Hulbert & Berghoff LLP

(57) ABSTRACT

In an example, a light control system includes a power converter and a UV light source. The power converter includes an input for receiving an input power from a power source during a time interval, a power buffer for storing power using the input power received at the input during a first portion of the time interval, and an output for outputting a supply power during a second portion of the time interval. The supply power includes a combination of power from (i) the input power received at the input during the second portion of the time interval and (ii) the power stored in the power buffer during the first portion of the time interval. The UV light source is configured to, using the supply power during the second portion of the time interval, emit UV light at an intensity providing a target level of antimicrobial efficacy.

20 Claims, 4 Drawing Sheets

(51) Int. Cl.
*A61L 2/26* (2006.01)
*A61L 9/20* (2006.01)
*H05B 41/28* (2006.01)
*A61L 2/24* (2006.01)

(52) U.S. Cl.
CPC ......... *H05B 37/0227* (2013.01); *H05B 41/28* (2013.01); *A61L 2202/11* (2013.01); *A61L 2202/14* (2013.01); *A61L 2202/25* (2013.01); *A61L 2209/111* (2013.01)

(58) Field of Classification Search
CPC ........... A61L 2202/25; A61L 2209/111; H05B 37/02; H05B 37/0227; H05B 33/08; H05B 41/32; G03F 7/70033; G03F 7/70525; H05G 2/005; H05H 1/04; H01J 61/80; B82Y 10/00
See application file for complete search history.

(56) References Cited

U.S. PATENT DOCUMENTS

| | | | |
|---|---|---|---|
| 6,877,248 | B1 | 4/2005 | Cross et al. |
| 8,084,752 | B2 | 12/2011 | Ranta et al. |
| 8,138,690 | B2 | 3/2012 | Chemel et al. |
| 8,339,069 | B2 | 12/2012 | Chemel et al. |
| 8,368,321 | B2 | 2/2013 | Chemel et al. |
| 8,543,249 | B2 | 9/2013 | Chemel et al. |
| 8,552,664 | B2 | 10/2013 | Chemel et al. |
| 8,593,135 | B2 | 11/2013 | Chemel et al. |
| 8,805,550 | B2 | 8/2014 | Chemel et al. |
| 8,954,170 | B2 | 2/2015 | Chemel et al. |
| 9,623,133 | B2 | 4/2017 | Childress et al. |
| 9,700,072 | B2 | 7/2017 | Dobrinsky et al. |
| 9,783,974 | B1 | 10/2017 | Tillotson |
| 9,855,353 | B1 | 1/2018 | Stacy |
| 10,145,055 | B1 | 12/2018 | Harlan et al. |
| 2005/0156541 | A1 | 7/2005 | Henze |
| 2006/0087259 | A1 | 4/2006 | Fiorello |
| 2006/0163135 | A1 | 7/2006 | Ellis et al. |
| 2007/0085487 | A1 | 4/2007 | Kuennen et al. |
| 2010/0193629 | A1 | 8/2010 | Breit et al. |
| 2011/0057123 | A1 | 3/2011 | Ho |
| 2011/0155915 | A1 | 6/2011 | Brueck et al. |
| 2012/0161629 | A1 | 6/2012 | Kim et al. |
| 2013/0330235 | A1 | 12/2013 | Stibich et al. |
| 2014/0059796 | A1* | 3/2014 | Boodaghians ............ A61L 2/10 15/339 |
| 2014/0266695 | A1 | 9/2014 | Addison et al. |
| 2016/0195427 | A1 | 7/2016 | Vance et al. |
| 2016/0220716 | A1 | 8/2016 | Childress et al. |
| 2016/0250362 | A1 | 9/2016 | Mackin |
| 2017/0107659 | A1 | 4/2017 | Hills |
| 2017/0283062 | A1 | 10/2017 | Childress |
| 2017/0283092 | A1 | 10/2017 | Brown |
| 2017/0284076 | A1 | 10/2017 | Jensen |
| 2019/0171111 | A1* | 6/2019 | Kimsey-Lin ........... B82Y 10/00 |

FOREIGN PATENT DOCUMENTS

| | | |
|---|---|---|
| JP | 2002263645 | 9/2002 |
| WO | 99/62567 | 12/1999 |
| WO | WO 2005/000365 | 1/2005 |
| WO | WO 2007/141562 | 12/2007 |
| WO | WO 2017/094483 | 6/2017 |

OTHER PUBLICATIONS

Co-pending U.S. Appl. No. 15/237,710, filed Aug. 16, 2016.
Co-pending U.S. Appl. No. 15/241,438, filed Aug. 19, 2016.
Co-pending U.S. Appl. No. 15/245,251, filed Aug. 24, 2016.
Co-pending U.S. Appl. No. 15/259,685, filed Sep. 8, 2016.
Co-pending U.S. Appl. No. 15/271,349, filed Sep. 21, 2016.
Co-pending U.S. Appl. No. 15/273,814, filed Sep. 23, 2016.
Co-pending U.S. Appl. No. 15/632,968, filed Jun. 26, 2017.
Co-pending U.S. Appl. No. 15/633,028, filed Jun. 26, 2017.
Co-pending U.S. Appl. No. 15/633,121, filed Jun. 26, 2017.
Co-pending U.S. Appl. No. 15/633,142, filed Jun. 26, 2017.

* cited by examiner

SYSTEMS AND METHODS FOR OPERATING A LIGHT SYSTEM

FIELD

The present disclosure generally relates to systems and methods for light systems, and more particularly to systems and methods for operating an ultraviolet (UV) light source to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using a UV light source. However, in some instances, the power required by the UV light source to achieve a target level of antimicrobial efficacy of the UV light may exceed the power that is supplied by a power source and/or an electrical infrastructure in the environment.

SUMMARY

In an example, a method of operating a UV light source is described. The method includes receiving, at an input of a power converter, an input power from a power source during a first portion of a time interval and a second portion of the time interval. The method also includes, during the first portion of the time interval, using the input power to store power in a power buffer. The method further includes, during the second portion of the time interval, outputting a supply power from an output of the power converter. The supply power includes a combination of power from (i) the input power received at the input during the second portion of the time interval and (ii) the power stored in the power buffer during the first portion of the time interval. The method also includes activating, using the supply power during the second portion of the time interval, the UV light source to emit UV light at an intensity providing a target level of antimicrobial efficacy. The input power received during the second portion of the time interval is insufficient by itself for activating the UV light source to emit the UV light at the intensity providing the target level of antimicrobial efficacy.

In another example, a light control system is described. The light control system includes a power converter and a UV light source. The power converter includes an input configured to receive an input power from a power source during a time interval, a power buffer configured to store power using the input power received at the input during a first portion of the time interval, and an output configured to output a supply power during a second portion of the time interval. The supply power includes a combination of power from (i) the input power received at the input during the second portion of the time interval and (ii) the power stored in the power buffer during the first portion of the time interval. The UV light source is configured to, using the supply power during the second portion of the time interval, emit UV light at an intensity providing a target level of antimicrobial efficacy. The input power received during the second portion of the time interval is insufficient by itself for the UV light source to emit the UV light at the intensity providing the target level of antimicrobial efficacy.

In another example, a light control system is described. The light control system includes a power converter configured to convert an input power received from a power source to a supply power. The supply power has a wattage that is greater than a wattage of the input power. The light control system also includes a UV light source configured to, using the supply power, emit UV light at an intensity providing a target level of antimicrobial efficacy. The wattage of the input power is insufficient by itself for the UV light source to emit the UV light at the intensity providing the target level of antimicrobial efficacy. The light control system further includes a light sensor and a control device. The light sensor is configured to measure an optical parameter of the UV light emitted by the UV light source. The optical parameter is related to a resonance of the power converter relative to the UV light source. The control device is communicatively coupled to the power converter and the light sensor. The control device is configured to: (i) receive, from the light sensor, a sensor signal indicating the optical parameter, and (ii) based on the optical parameter indicated by the sensor signal, provide a feedback signal to the power converter to tune the power converter to a frequency of the UV light source.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Figure 1:
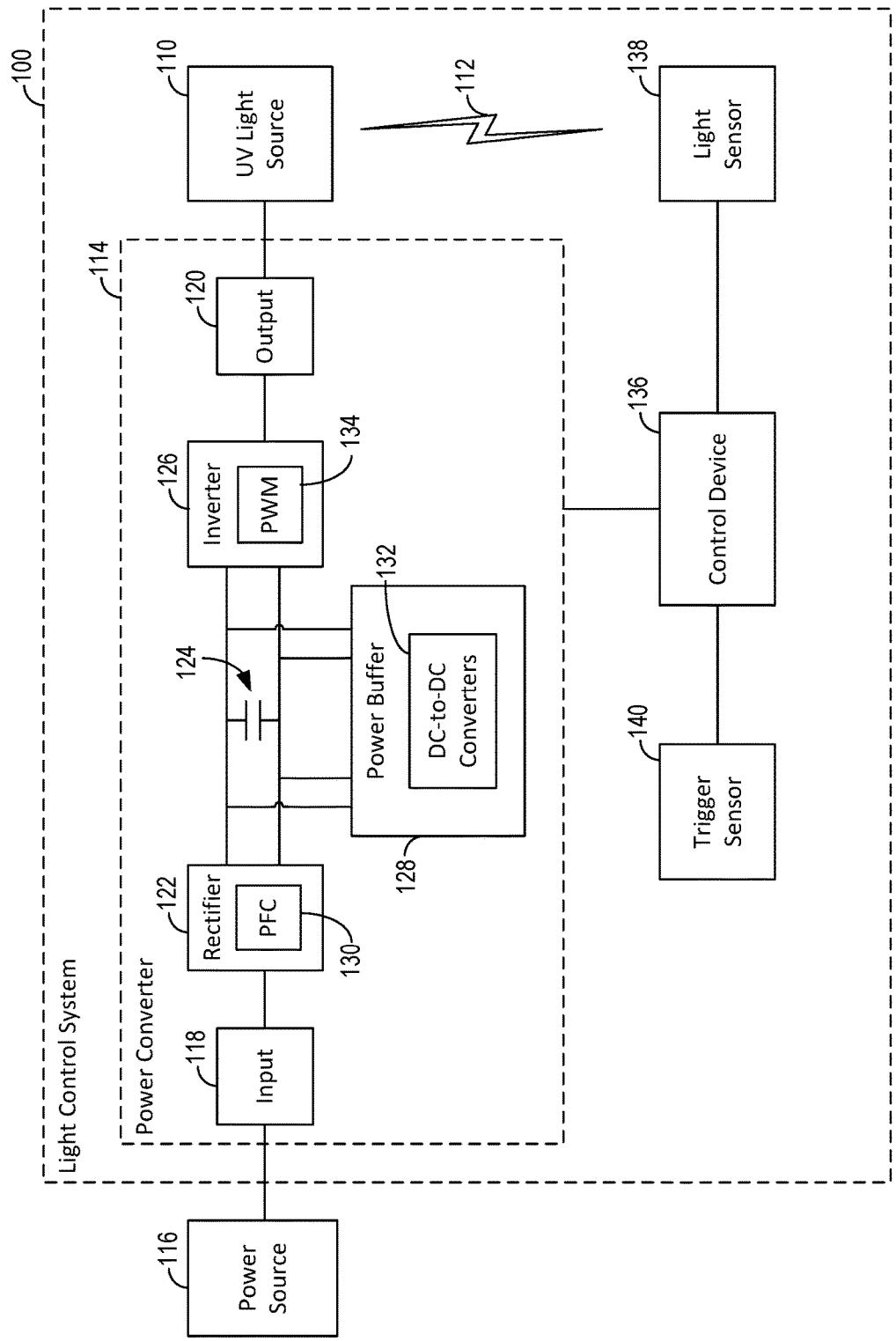
FIG. 1 illustrates a simplified block diagram of a light control system according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide light control systems and methods for operating a UV light source to achieve a target level of antimicrobial efficacy in a limited-power environment. When activated during an activation cycle, the UV light source emits UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

The antimicrobial efficacy of the UV light during the activation cycle is related to factors such as, for instance, the length of time a microorganism is exposed to the UV light (i.e., the "exposure time"), the intensity of the UV light, and the wavelength of the UV light. As one example, the antimicrobial efficacy of the UV light at a particular wavelength can be specified as a UV dose, which can be determined based on an equation having the general form of:

$$\text{UV dose} = \text{UV light intensity} \times \text{exposure time} \quad (\text{eq. 1})$$

where the UV dose is specified in mWs/cm$^2$, the UV light intensity is specified in mW/cm$^2$ at a predetermined distance (e.g., one meter) from the UV light source, and the exposure time is specified in seconds.

Because the UV light source converts electrical power into the UV light, the UV light source may require at least a threshold amount of power to emit the UV light at the intensity and/or for the exposure time providing the target level of antimicrobial efficacy. The threshold amount of power required to emit the UV light at the target level of antimicrobial efficacy may be based on characteristics of the UV light source such as, for example, a type of UV light source, and/or a size of the UV light source.

In a limited-power environment, a power source and/or an electrical distribution system may provide a power that is insufficient by itself for activating the UV light source to emit the UV light at the target level of antimicrobial efficacy. In one example, the UV light source can be coupled to a power source, which is configured to generate a power that is less than the threshold amount of power required by the UV light source to emit the UV light at the target level of antimicrobial efficacy. For instance, the UV light source can be installed in an environment in which it is desirable to reduce (or minimize) the size and/or weight of the power source.

In another example, the power source may be configured to generate a sufficient amount of power, but an electrical distribution system may supply portions of the generated power to other systems as well such that only an insufficient portion of the power is available to the UV light source. For instance, a vehicle can have an electrical distribution system that provides specific portions of a power supplied by a power source to various subsystems of the vehicle in accordance with a power budget. In this way, each subsystem receives an amount of power that is sufficient to meet its needs. A problem is presented, however, when the vehicle is to be retrofitted with the UV light source as the power requirements of the UV light source may not have been taken into consideration when the power budget and electrical distribution system were designed.

The example systems and methods described herein can beneficially overcome challenges to operating the UV light source at the target level of antimicrobial efficacy in a limited-power environment. Within examples, a light control system can receive an input power from a power source during a time interval. A UV light source of the light control system is deactivated during a first portion of the time interval, and the UV light source is activated to emit UV light during a second portion of the time interval. However, the input power received during the second portion of the time interval is insufficient by itself for activating the UV light source to emit the UV light at the target level of antimicrobial efficacy.

To address this limitation of the input power, the light control system can store the input power in a power buffer during the first portion of the time interval. Later, during the second portion of the time interval, the light control system can provide to the UV light source a supply power that combines (i) the input power received during the second portion of the time interval and (ii) the power stored in the power buffer during the first portion of the time interval. The combination of power is sufficient for activating the UV light source to emit the UV light at the target level of antimicrobial efficacy.

Also, within examples, the light control system can beneficially measure the UV light emitted by the UV light source and provide feedback to enhance (or maximize) efficient use by the UV light source of the supply power. For instance, the light control system can include a light sensor that senses the emitted UV light and measures an optical parameter, which is related to a resonance of a power converter relative to the UV light source. Based on the measured optical parameter of the UV light, a control device can provide a feedback signal to cause the power converter to operate in resonance with the UV light source. By operating the power converter in resonance with the UV light source, the supply power can be more efficiently converted into UV light. As such, the dynamic feedback control can enhance the level of antimicrobial efficacy of the UV light, and/or allow for the size and/or weight of the power buffer to be reduced (or minimized).

Within examples, the light control system described herein can be located in any environment having a power supply, which can benefit from disinfection. For instance, the light control system can be in a vehicle (e.g., an aircraft, a boat, a train, and/or an automobile), a medical environment (e.g., a hospital, a doctor office, and/or other healthcare facility), a restaurant, an office, and/or a household. In one implementation, the light control system can be located in a lavatory of a vehicle.

Referring now to FIG. 1, a light control system 100 is depicted according to an example embodiment. As shown in FIG. 1, the light control system 100 includes a UV light source 110. When activated, the UV light source 110 can emit UV light 112 to provide a target level of antimicrobial efficacy. For instance, the UV light source 110 can emit the UV light 112 at a predetermined wavelength and intensity for a predetermined exposure time to achieve the target level of antimicrobial efficacy during an activation cycle. In one example, the UV light source 110 can emit the UV light 112 at an intensity of 10 mW/cm$^2$ for an exposure time of 10 seconds to achieve the target level of antimicrobial efficacy for the activation cycle.

Also, as examples, the UV light source 110 can include one or more excimer bulbs, mercury-vapor lamps, downshifting phosphor lamps, and/or light emitting diodes (LEDs). More generally, the UV light source 110 can be a light source that emits the UV light 112 at a wavelength within the UV spectrum (i.e., between approximately 10 nanometers (nm) and approximately 400 nm). In some implementations, the UV light source 110 can be a light source that emits UV light 112 at a wavelength within the far-UV spectrum (e.g., between approximately 190 nm and approximately 240 nm). For instance, in one implementation, the UV light source 110 can be a light source that emits the UV light 112 at a wavelength of approximately 222 nm. By emitting the UV light 112 at a wavelength in the far-UV spectrum, the UV light source 110 can more rapidly disinfect the environment than by emitting the UV light 112 at other wavelengths in the UV spectrum.

As shown in FIG. 1, the light control system 100 also includes a power converter 114 coupled to the UV light source 110. The power converter 114 receives an input power from a power source 116 at an input 118 and outputs a supply power to the UV light 112 source at an output 120. As an example, the power source 116 can provide the input power as an alternating current (AC) power. In one implementation, the power source 116 can provide the input power as a three-phase AC power with a voltage of 115 volts (V) and a frequency of 400 Hertz (Hz). For instance, in a vehicle, the power source 116 can include an engine turbine that generates electrical energy and an electrical distribution system that provides the generated electrical energy to the light control system 100 in the form of the input power. Other example power sources 116 are also possible.

The power converter 114 converts the input power into the supply power. Within examples, the supply power can have a different AC waveform than the input power. For instance, the supply power can have a different frequency, voltage, and/or current than the input power. More generally, the supply power can have a wattage that is greater than a wattage of the input power. As such, the power converter 114 can provide the UV light source 110 with the supply power, which is sufficient to emit the UV light 112 at the target level of antimicrobial efficacy. In one example, the input power can have a wattage that is less than 1 kW and the supply power can have a wattage that is equal to or greater than 1 kW.

In FIG. 1, the power converter 114 includes the input 118, a rectifier 122, a direct current (DC) link 124, an inverter 126, a power buffer 128, and the output 120. The rectifier 122 is coupled to and receives the input power from the input 118. The rectifier 122 can convert the AC input power into a DC power. In an example, the rectifier 122 include a power factor corrector (PFC) 130 that corrects a power factor of the input power to facilitate more efficient use of the input power by the light control system 100. The PFC 130 can also facilitate isolating the light control system 100 from the power source 116 (and/or other electrical subsystems coupled to the power source 116). Within examples, the PFC 130 can include a passive PFC circuit, an active PFC circuit, and/or a dynamic PFC circuit.

The rectifier 122 is coupled to the inverter 126 via the DC link 124. As described in further detail below, when the light source 110 is activated, the inverter 126 converts the DC power received from the rectifier 122 into an AC power, which provides a portion of the supply power at the output 120. The DC link 124 facilitates the coupling of the rectifier 122 and the inverter 126. In one example, the DC link 124 can include a capacitor coupled in parallel between the rectifier 122 and the inverter 126. The DC link 124 can assist in mitigating transients propagating toward the power source 116 and/or assist in smoothing pulses in the rectified DC power provided by the rectifier 122.

As shown in FIG. 1, the power buffer 128 is coupled in parallel between the rectifier 122 and the DC link 124, and between the DC link 124 and the inverter 126. The power buffer 128 stores power using the input power received at the input 118 when the UV light source 110 deactivated. As examples, the power buffer 128 can include a battery, a capacitor, and/or another type of energy storage device.

In the example of FIG. 1, the power buffer 128 includes a plurality of DC-to-DC converters 132 coupled to each other. When the UV light source 110 is deactivated, the DC-to-DC converters 132 receive the DC power from the rectifier 122. In one implementation, the DC-to-DC converters 132 include a first DC-to-DC converter that steps down the DC power received from the rectifier 122 and a second DC-to-DC converter that steps up the DC power. This configuration of the DC-to-DC converters 132 can beneficially reduce (or minimize) the size and/or weight of the power buffer 128.

As noted above, inverter 126 is coupled to the rectifier 122 and the power buffer 128. In this arrangement, when the light source 110 is activated, the inverter 126 can receive the DC power from the rectifier 122 and the power stored in the power buffer 128. The inverter 126 can convert this combination of DC power from the rectifier 122 and the power buffer 128 into the supply power, which has an AC waveform. In an example, the inverter 126 can include a pulse-width modulator (PWM) 134, which can switch on and off to control a frequency of the supply power. In another example, the inverter 126 can additionally or alternatively include a sine wave generator and/or a carrier wave generator to convert the combination of DC power to the supply power.

As further shown in FIG. 1, the light control system 100 can also include a control device 136 communicatively coupled to the power converter 114 and a light sensor 138. The light sensor 138 can sense the UV light 112 emitted by the UV light source 110, measure an optical parameter of the sensed UV light 112, and provide a sensor signal to the control device 136 indicating the optical parameter measured by the light sensor 138. Accordingly, the light sensor 138 can be positioned such that a portion of the UV light 112 emitted by the light source 110 is incident on the light sensor 138. As examples, the light sensor 138 can include one or more photodiodes, photojunction devices, light dependent resistors (LDRs), and/or photoconductive cells to sense and measure the optical parameter of the UV light 112.

The control device 136 can receive the sensor signal from the light sensor 138, and compare the optical parameter indicated by the sensor signal to a target optical parameter. The target optical parameter can be a fixed value and/or an adjustable value. Based on the comparison, the control device 136 can provide a feedback signal to the power converter 114 to cause the power converter 114 to adjust an electrical parameter of the supply power. For instance, the electrical parameter can be the frequency and/or the pulse width of the AC waveform of the supply power, and the feedback signal can thus cause the PWM 134 to switch of and off based on the feedback signal to adjust the frequency and/or the pulse-width of the AC waveform of the supply power.

In an example, the optical parameter measured by the light sensor 138 is related to a resonance of the power converter 114 relative to the UV light source 110. For instance, when the UV light source 110 is activated using the supply power, a gas in the UV light source 110 can undergo a process of ion formation and ion recombination, which can define a frequency of the light source 110. When the AC waveform of the supply power has a frequency and/or pulse width that is resonant with the frequency of the light source 110, the intensity of the UV light 112 emitted by the UV light source 110 is at a maximum intensity consistent with the input power received at the input 118.

Within examples, the light sensor 138 can measure the irradiance of the UV light 112 as an indication of the resonance of the power converter 114 relative to the UV light source 110. For instance, based on one or more characteristics of the power converter 114 and/or the light source 110, the irradiance of the UV light 112 can be expected to have a target irradiance when the power converter 114 is in resonance with the UV light source 110 (i.e., when the frequency and/or pulse width of the supply power is in resonance with the frequency of the UV light source 110). The control device 136 can thus compare the irradiance indicated by the sensor signal to the target irradiance and, based on the comparison, the control device 136 can provide the feedback signal to the power converter 114 to tune the power converter 114 to the frequency of the UV light source 110. Because the frequency of the light source 110 may drift over time, the control device 136 and the light sensor 138 can dynamically adjust operation of the power converter 114 to maintain the power converter 114 in resonance with the light source 110 over a plurality of activation cycles of the UV light source 110 (e.g., over the life of the UV light source 110).

Further, by tuning the power converter 114 to the frequency of the UV light source 110, the efficiency of the UV light source 110 can be increased (or maximized). In turn, this can allow for the power buffer 128 to be relatively smaller and/or lighter as less power may need to be stored in the power buffer 128 to meet the power requirements of the light source 110 for emitting the UV light 112 at the target level of antimicrobial efficacy.

As noted above, the target optical parameter can be a fixed value in one example. In an alternative example, the target optical parameter can be adjustable. For instance, the control device 136 can iteratively adjust the target optical parameter using one or more previously measured optical parameters to maintain the measured irradiance at a peak value.

In FIG. 1, the control device 136 can also control activating and deactivating the UV light source 110. For example, the control device 136 can be coupled to one or more trigger sensors 140 that can detect one or more trigger conditions and responsively generate a trigger-sensor signal indicating that the trigger condition(s) were detected. The control device 136 can (i) receive the trigger-sensor signal indicating that the trigger condition was detected, (ii) determine, based on the trigger-sensor signal, that one or more criteria are met, and (iii) responsive to the determination that the one or more criteria are met, transmit a control signal to activate the UV light source 110.

In an example, the trigger sensor(s) 140 can include a motion sensor, an occupancy sensor, a thermal sensor, an open/close sensor, an infrared sensor device, an ultrasonic sensor device, a floor pressure sensor, and/or other types of sensors. For instance, in an example in which the light control system 100 is located on a vehicle having a lavatory, the trigger condition(s) detected by the trigger sensor(s) 140 can include a door of the lavatory being opened, the door of the lavatory being closed, the lavatory being occupied, and/or the lavatory being unoccupied. Additionally, for example, the one or more criteria that is used by the control device 136 to determine whether to activate the UV light source 110 can include one or more criterion such as a door of the lavatory being closed, the lavatory being unoccupied, the lavatory having been occupied a predetermined number of times since a previous activation of the UV light source 110, and/or a predetermined amount of time having passed since the previous activation of the UV light source 110.

In an additional or alternative example, the trigger sensor(s) 140 can include a sensor for measuring the amount of power stored in the power buffer 128. In such example, the trigger sensor(s) 140 can generate the trigger-sensor signal to indicate the amount of power is stored in the power buffer 128, and the control device 136 can determine whether the indicated amount of power is sufficient to activate the UV light source 110 at the target level of antimicrobial efficacy during an activation cycle. For instance, the control device 136 can compare the amount of power indicated by the trigger-sensor signal to a threshold amount of power stored in the control device 136. Responsive to the control device 136 determining that the indicated amount of power is greater than the threshold amount of power, the control device 136 can transmit the control signal to the power converter 114 to activate the UV light source 110. Whereas, responsive to the control device 136 determining that the indicated amount of power is less than the threshold amount of power, the control device 136 can continue to wait until the power buffer 128 has at least the threshold amount of power before transmitting the control signal.

In general, the control device 136 is a computing device that is configured to control operation of the light control system 100. As such, the control device 136 can be implemented using hardware, software, and/or firmware. For example, the control device 136 can include one or more processors and a non-transitory computer readable medium (e.g., volatile and/or non-volatile memory) that stores machine language instructions or other executable instructions. The instructions, when executed by the one or more processors, cause the light control system 100 to carry out the various operations described herein. The control device 136, thus, can receive data (including data indicated by the sensor signals and/or trigger-sensor signals) and store the data in memory as well.

In operation, the light control system 100 receives, at the input 118 of the power converter 114, the input power from the power source 116 during a first portion of a time interval and a second portion of the time interval. The UV light source 110 is deactivated during the first portion of the time interval. The UV light source 110 is activated during the second portion of the time interval. However, the input power received during the second portion of the time interval is insufficient by itself for the UV light source 110 to emit the UV light 112 at the intensity and/or for the exposure time providing the target level of antimicrobial efficacy.

While the UV light source 110 is deactivated during the first portion of the time interval, the rectifier 122 converts the input power to the DC power and the DC power is stored in the power buffer 128. After the first portion of the time interval, the control device 136 can activate the UV light source 110 during the second portion of the time interval. For example, the control device 136 can activate the UV light source 110 responsive to the trigger sensor(s) 140 detecting the trigger condition(s) and the control device 136 determining, based at least in part on the trigger-sensor signal received from the trigger sensor(s) 140, that the criteria for activating the UV light source 110 are met.

During the second portion of the time interval, the power converter 114 outputs the supply power from the output 120 to the UV light source 110. The UV light source 110 can use the supply power during the second portion of the time interval to emit the UV light 112 at the intensity and/or for the exposure time providing the target level of antimicrobial efficacy.

As noted above, the supply power can include a combination of power from (i) the input power received at the input 118 during the second portion of the time interval, and (ii) the power stored in the power buffer 128 during the first portion of the time interval. For instance, when the UV light source 110 is activated during the second portion of the time interval, the rectifier 122 can convert the input power to the DC power and provide the DC power to the inverter 126. Additionally, when the UV light source 110 is activated during the second portion of the time interval, the power buffer 128 can sense a voltage droop and responsively provide the power stored in the power buffer 128 to the inverter 126. The inverter 126 thus receives the DC power from the rectifier 122 and the stored power from the power buffer 128, and converts this combination of power into the supply power. By combining the input power received at the input 118 during the second portion of the time interval and the power stored in the power buffer 128, the power converter 114 can provide the UV light source 110 with a power that is sufficient to activate the UV light source 110 at the target level of antimicrobial efficacy.

Additionally, during the second portion of the time interval, the light sensor 138 can sense a portion of the UV light 112 emitted by the light source 110 and measure an optical parameter of the UV light 112. The optical parameter can relate to the resonance of the power converter 114 relative to the UV light source 110. The light sensor 138 can transmit the sensor signal indicating the measured optical parameter to the control device 136. The control device 136 can then perform a comparison of the optical parameter indicated by the sensor signal to the target optical parameter. Based on the comparison, the control device 136 can provide a feedback signal to the power converter 114 to tune the power converter 114 to the frequency of the UV light source 110 so that the power converter 114 and the light source 110 can be in resonance for a remainder of the current activation cycle and/or a next activation cycle of the UV light source 110.

In one example, the target level of antimicrobial efficacy can be defined by an intensity of 10 mW/cm$^2$ intensity and an exposure time of 10 seconds. In this example, the input 118 can receives the input power as a three-phase AC power with a voltage of approximately 115 $V_{AC}$, a frequency of approximately 400 Hz, and a current of 0.5 Amps (A) such that the input power has a wattage of approximately 100 W (i.e., less than 1 kW). As such, the input power is insufficient by itself to activate the UV light source 110 at the target level of antimicrobial efficacy. The rectifier 122 can convert the input power to the DC power having a voltage of approximately 200 $V_{DC}$ and a current of approximately 0.5 A. The power buffer 128 can include a first DC-to-DC converter that steps down the DC power from 200 $V_{DC}$ to 28 $V_{DC}$, and a second DC-to-DC converter that steps the DC power from 28 $V_{DC}$ to 200 $V_{DC}$.

In this arrangement, during the first portion of the time interval, the rectifier 122 converts the input power to the 200 $V_{DC}$ power and the power buffer 128 stores the 200 $V_{DC}$ power. During the second portion of the time interval, the rectifier 122 converts the input power to the 200 $V_{DC}$ power and provides the 200 $V_{DC}$ power to the inverter 126. Also, during the second portion of the time interval, the power buffer 128 provides the stored power to the inverter 126 with a voltage of approximately 200 $V_{DC}$ and a current of approximately 5 A. As a result, the inverter 126 receives the combination of power at 200 $V_{DC}$ and a current of at least 5 A such that the supply power has a wattage equal to or greater than 1 kW. In this example, the power buffer 128 can have an energy storage capacity at least large enough to provide the stored power at 200 $V_{DC}$ and 5 A for the 10 second exposure time. In this way, the power converter 114 can provide the UV light source 110 with sufficient power to achieve the target level of antimicrobial efficacy during the activation cycle of the UV light source 110.

In the example described above, the target level of antimicrobial efficacy is UV dose of approximately 10 mWs/cm$^2$. In additional or alternative examples, the target level of antimicrobial efficacy can be a UV dose between approximately 2 mWs/cm$^2$ and approximately 500 mWs/cm$^2$. Different microorganisms may have different abilities to withstand exposure to the UV light 112. In some implementations, the target level of antimicrobial efficacy can be based on a target microorganism-kill rate for one or more types of microorganisms that are targeted for disinfection by the light control system 100. As examples, the targeted microorganism-kill rate can be approximately 80%, approximately 90%, approximately 95%, approximately 99%, approximately 99.9%, and/or approximately 99.99% of the one or more target organisms irradiated by the UV dose.

Additionally, in the example described above, the power stored in the power buffer 128 provides approximately 90% of the supply power and the input power received during the second portion of the time interval provides approximately 10% of the supply power. In additional or alternative examples, the input power received during the second portion of time can provide approximately 5% to approximately 95% of the supply power and the power stored in the power buffer 128 can provide the remainder of the supply power.

Figure 2:
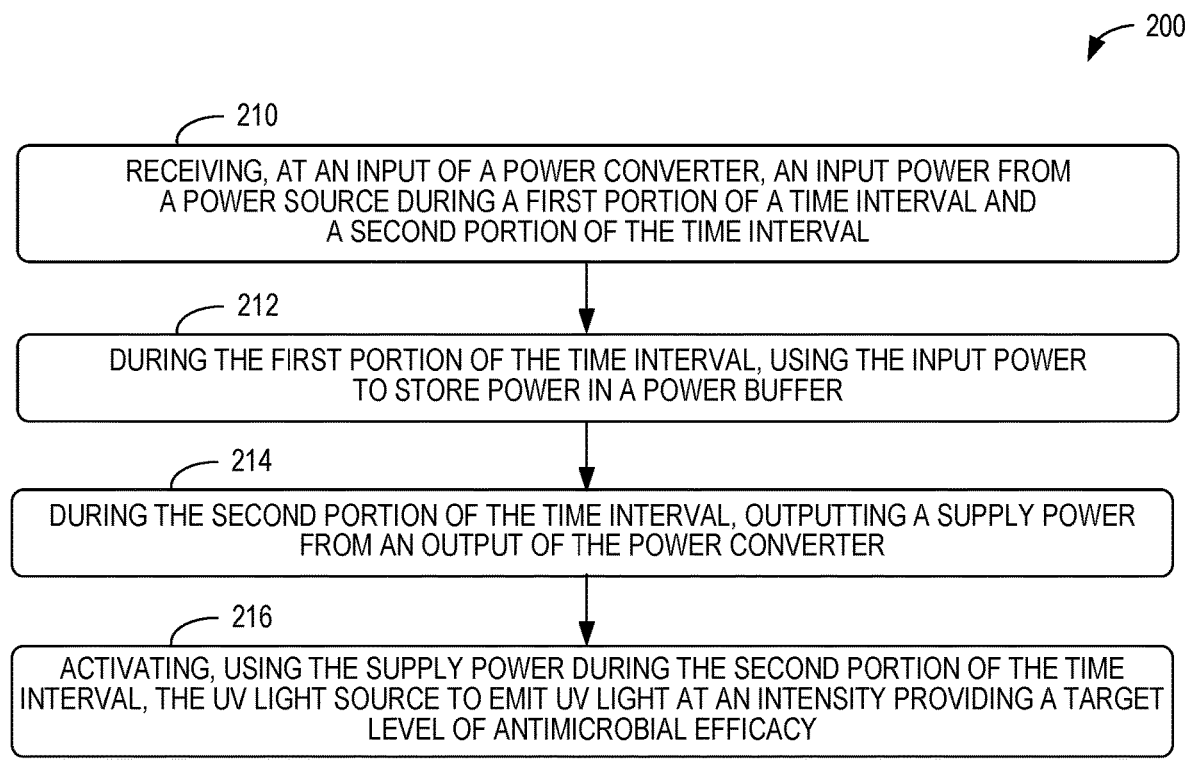
FIG. 2 illustrates a flow chart of an example process for operating a UV light source according to an example embodiment.

Referring now to FIG. 2, a flowchart for a process 200 of operating a UV light source is illustrated according to an example embodiment. As shown in FIG. 2, at block 210, the process 200 includes receiving, at an input of a power converter, an input power from a power source during a first portion of a time interval and a second portion of the time interval. At block 212, during the first portion of the time interval, the process 200 includes using the input power to store power in a power buffer. At block 214, during the second portion of the time interval, the process 200 includes outputting a supply power from an output of the power converter. The supply power includes a combination of power from (i) the input power received at the input during the second portion of the time interval and (ii) the power stored in the power buffer during the first portion of the time interval. At block 216, the process 200 includes activating, using the supply power during the second portion of the time interval, the UV light source to emit UV light at an intensity providing a target level of antimicrobial efficacy. For the process 200, the input power received during the second portion of the time interval is insufficient by itself for activating the UV light source to emit the UV light at the intensity providing the target level of antimicrobial efficacy.

Figure 3:
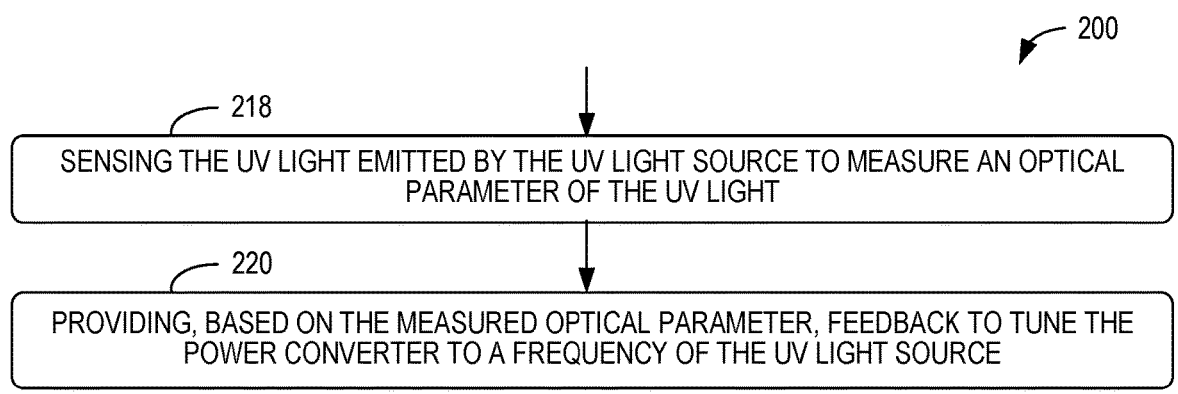
FIG. 3 illustrates a flow chart of an example process for operating a UV light source that can be used with the process shown in FIG. 2.

FIGS. 3-8 depict additional aspects of the process according to further examples. As shown in FIG. 3, the process 200 can further include sensing the UV light emitted by the UV light source to measure an optical parameter of the UV light at block 218. In an example, the optical parameter can be related to a resonance of a power converter relative to the UV light source. At block 220, the process 200 can include providing, based on the measured optical parameter, feedback to tune the power converter to a frequency of the UV light source.

Figure 4:
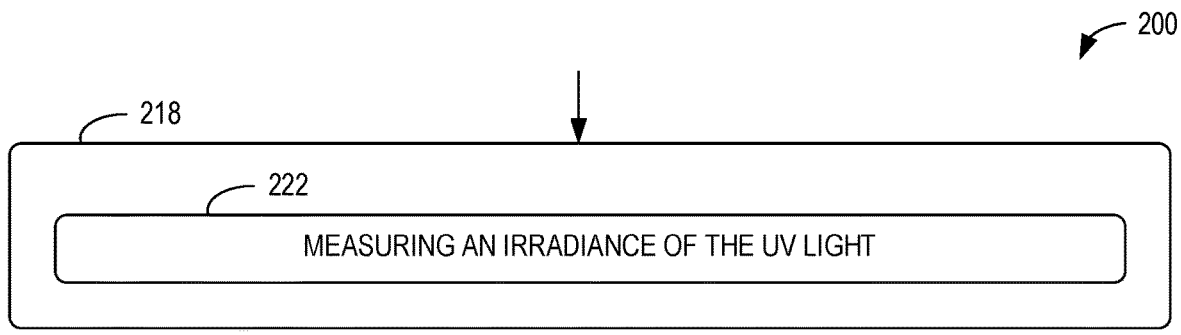
FIG. 4 illustrates a flow chart of an example process for operating a UV light source that can be used with the process shown in FIG. 3.
Figure 5:
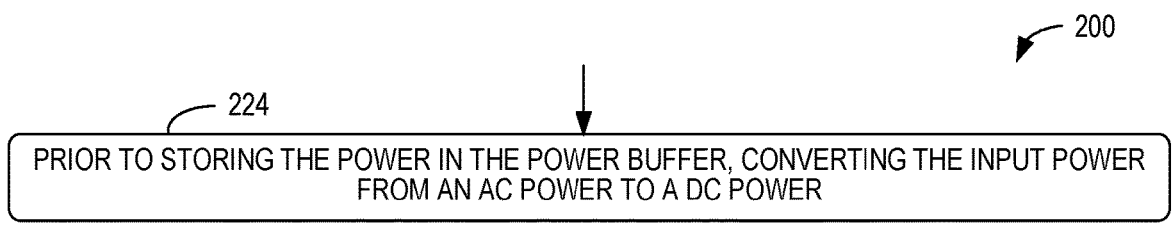
FIG. 5 illustrates a flow chart of an example process for operating a UV light source that can be used with the process shown in FIGS. 2-4.
Figure 6:
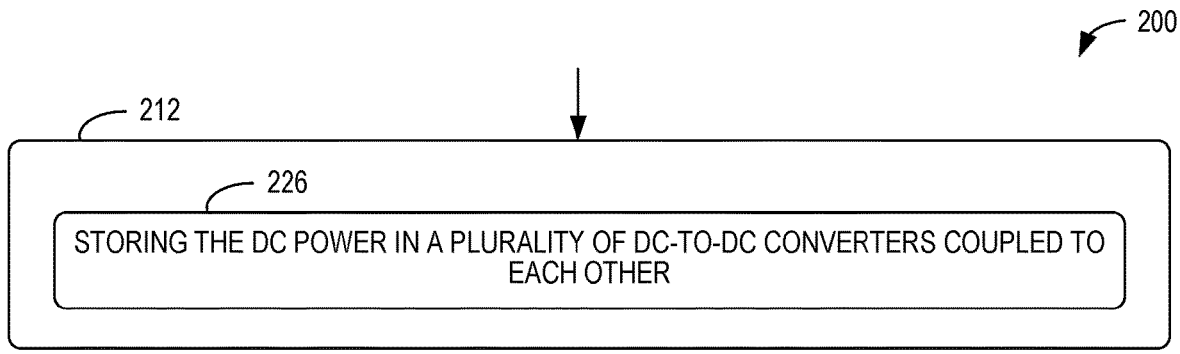
FIG. 6 illustrates a flow chart of an example process for operating a UV light source that can be used with the process shown in FIG. 5.
Figure 7:
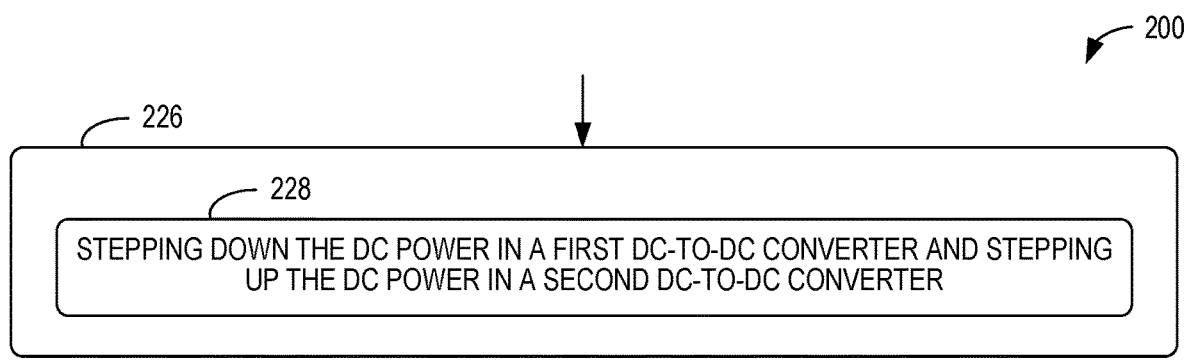
FIG. 7 illustrates a flow chart of an example process for operating a UV light source that can be used with the process shown in FIG. 6.
Figure 8:
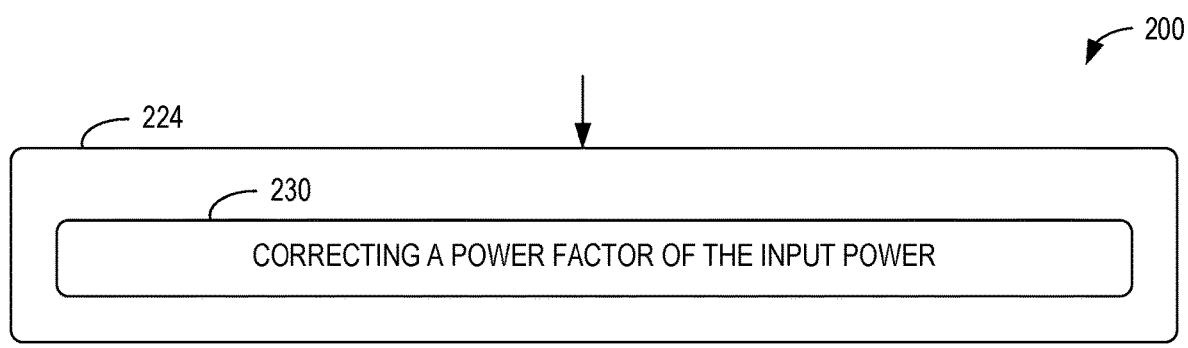
FIG. 8 illustrates a flow chart of an example process for operating a UV light source that can be used with the process shown in FIGS. 5-7.

As shown in FIG. 4, sensing the UV light to measure the optical parameter at block 218 can include measuring an irradiance of the UV light at block 222. As shown in FIG. 5, the process 200 can include, prior to storing the power in the power buffer, converting the input power from an AC power to a DC power. As shown in FIG. 6, storing the power in the power buffer at block 212 can include storing the DC power in a plurality of DC-to-DC converters coupled to each other at block 226. As shown in FIG. 7, storing the DC power in the plurality of DC-to-DC converters at block 226 can include stepping down the DC power in a first DC-to-DC converter and stepping up the DC power in a second DC-to-DC converter at block 228. As shown in FIG. 8, converting the input power at block 224 can include correcting a power factor of the input power at block 230.

The process 200 can be a linear and/or a non-linear process. Any of the blocks shown in FIGS. 2-8 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A method of operating a ultraviolet (UV) light source, comprising:
   receiving, at an input of a power converter, an input power from a power source during a first portion of a time interval and a second portion of the time interval;
   during the first portion of the time interval, using the input power to store power in a power buffer;
   during the second portion of the time interval, outputting a supply power from an output of the power converter, wherein the supply power comprises a combination of power from (i) the input power received at the input during the second portion of the time interval and (ii) the power stored in the power buffer during the first portion of the time interval; and
   activating, using the supply power during the second portion of the time interval, the UV light source to emit UV light at an intensity providing a target level of antimicrobial efficacy, and
   wherein the input power received during the second portion of the time interval is insufficient for activating the UV light source to emit the UV light at the intensity providing the target level of antimicrobial efficacy.

2. The method of claim 1, further comprising:
   sensing the UV light emitted by the UV light source to measure an optical parameter of the UV light, wherein the optical parameter is related to a resonance of a power converter relative to the UV light source; and
   providing, based on the measured optical parameter, feedback to tune the power converter to a frequency of the UV light source.

3. The method of claim 2, wherein sensing the UV light to measure the optical parameter comprises measuring an irradiance of the UV light.

4. The method of claim 1, wherein the intensity is a maximum intensity of the UV light source.

5. The method of claim 1, further comprising:
   prior to storing the power in the power buffer, converting the input power from an alternating current (AC) power to a direct current (DC) power.

6. The method of claim 5, wherein storing the power in the power buffer comprises storing the DC power in a plurality of DC-to-DC converters coupled to each other.

7. The method of claim 6, wherein storing the DC power in the plurality of DC-to-DC converters comprises stepping down the DC power in a first DC-to-DC converter and stepping up the DC power in a second DC-to-DC converter.

8. The method of claim 5, wherein converting the input power further comprises correcting a power factor of the input power.

9. The method of claim 1, wherein emitting the UV light from the UV light source comprises emitting the UV light at a wavelength of approximately 150 nm to approximately 240 nm.

10. A light control system, comprising:
    a power converter comprising:
      an input configured to receive an input power from a power source during a time interval,
      a power buffer configured to store power using the input power received at the input during a first portion of the time interval,
      an output configured to output a supply power during a second portion of the time interval, wherein the supply power comprises a combination of power from (i) the input power received at the input during the second portion of the time interval and (ii) the power stored in the power buffer during the first portion of the time interval; and an ultraviolet (UV) light source configured to, using the supply power during the second portion of the time interval, emit UV light at an intensity providing a target level of antimicrobial efficacy, wherein the input power received during the second portion of the time interval is insufficient for the UV light source to emit the UV light at the intensity providing the target level of antimicrobial efficacy.

11. The light control system of claim 10, further comprising:

a light sensor configured to measure an optical parameter of the UV light emitted by the UV light source, wherein the optical parameter is related to a resonance of the power converter relative to the UV light source; and a control device communicatively coupled to the power converter and the light sensor, wherein the control device is configured to:

receive, from the light sensor, a sensor signal indicating the optical parameter, perform a comparison of the optical parameter indicated by the sensor signal to a target optical parameter, and based on the comparison, provide a feedback signal to the power converter to tune the power converter to a frequency of the UV light source.

12. The light control system of claim 11, wherein the optical parameter comprises an irradiance of the UV light.

13. The light control system of claim 10, wherein the intensity is a maximum intensity of the UV light source.

14. The light control system of claim 10, wherein the input power is an alternating current (AC) power, and wherein the power converter comprises a rectifier configured to convert the input power to a direct current (DC) power.

15. The light control system of claim 14, wherein the rectifier comprises a power factor corrector (PFC) configured to correct a power factor of the input power.

16. The light control system of claim 14, wherein the power buffer comprises a plurality of DC-to-DC converters coupled to each other and configured to receive the DC power from the rectifier.

17. The light control system of claim 16, wherein the plurality of DC-to-DC converters comprises a first DC-to-DC converter and a second DC-to-DC converter, wherein the first DC-to-DC converter is configured to step down the DC power, and wherein the second DC-to-DC converter is configured to step up the DC power.

18. The light control system of claim 14, wherein the power converter further comprises an inverter configured to, during the second portion of the time interval:

receive the DC power from the rectifier;

receive the power stored in the power buffer; and convert the DC power received from the rectifier and the power received from the power buffer to the supply power, wherein the supply power is an AC power.

19. The light control system of claim 18, wherein the inverter comprises a pulse-width modulator.

20. A light control system, comprising:

a power converter configured to convert an input power received from a power source to a supply power, wherein the supply power has a wattage that is greater than a wattage of the input power;

an ultraviolet (UV) light source configured to, using the supply power, emit UV light at an intensity providing a target level of antimicrobial efficacy, wherein the wattage of the input power is insufficient for the UV light source to emit the UV light at the intensity providing the target level of antimicrobial efficacy;

a light sensor configured to measure an optical parameter of the UV light emitted by the UV light source, wherein the optical parameter is related to a resonance of the power converter relative to the UV light source; and a control device communicatively coupled to the power converter and the light sensor, wherein the control device is configured to:

receive, from the light sensor, a sensor signal indicating the optical parameter, and based on the optical parameter indicated by the sensor signal, provide a feedback signal to the power converter to tune the power converter to a frequency of the UV light source.

* * * * *